United States Patent
Chen et al.

(10) Patent No.: US 8,000,922 B2
(45) Date of Patent: Aug. 16, 2011

(54) METHODS AND SYSTEMS FOR GENERATING INFORMATION TO BE USED FOR SELECTING VALUES FOR ONE OR MORE PARAMETERS OF A DETECTION ALGORITHM

(75) Inventors: Hong Chen, San Ramon, CA (US); Michael J. Van Riet, Morgan Hill, CA (US); Chien-Huei (Adam) Chen, San Jose, CA (US); Jason Z. Lin, Saratoga, CA (US); Chris Maher, Campbell, CA (US); Michal Kowalski, Santa Cruz, CA (US); Barry Becker, San Jose, CA (US); Stephanie Chen, Fremont, CA (US); Subramanian Balakrishnan, Cupertino, CA (US); Suryanarayana Tummala, Andhra Pradesh (IN)

(73) Assignee: KLA-Tencor Corp., San Jose, CA (US)

( * ) Notice: Subject to any disclaimer, the term of this patent is extended or adjusted under 35 U.S.C. 154(b) by 569 days.

(21) Appl. No.: 12/128,979

(22) Filed: May 29, 2008

(65) Prior Publication Data
US 2009/0299681 A1  Dec. 3, 2009

(51) Int. Cl.
*H01L 21/66* (2006.01)
(52) U.S. Cl. ........ 702/123; 702/127; 702/155; 702/134; 378/137; 356/237.4; 356/237.5
(58) Field of Classification Search ............... 702/127, 702/123, 155, 35, 36, 40, 75–77, 117, 118, 702/183, 185, 189, 134, 135; 378/56, 58, 378/62, 137; 703/18; 250/363.02, 310, 307, 250/311; 356/237.4, 237.5
See application file for complete search history.

(56) References Cited

U.S. PATENT DOCUMENTS
6,985,220 B1 * 1/2006 Chen et al. ............... 356/237.5
(Continued)

FOREIGN PATENT DOCUMENTS
JP   2004-177139   6/2004
(Continued)

OTHER PUBLICATIONS

U.S. Appl. No. 60/974,030 (Bhaskar et al.) entitled Systems and Methods for Creating Persistent Data for a Wafer and for Using Persistent Data for Inspection-Related Functions filed on Sep. 20, 2007.

(Continued)

*Primary Examiner* — Carol S Tsai
(74) *Attorney, Agent, or Firm* — Ann Marie Mewherter (57) ABSTRACT

Methods and systems for generating information to be used for selecting values for parameter(s) of a detection algorithm are provided. One method includes without user intervention performing a scan of an area of a wafer using an inspection system and default values for parameter(s) of a detection algorithm to detect defects on the wafer. The method also includes selecting a portion of the defects from results of the scan based on a predetermined maximum number of total defects to be used for selecting values for the parameter(s) of the detection algorithm. The method further includes storing information, which includes values for the parameter(s) of the detection algorithm determined for the defects in the portion. The information can be used to select the values for the parameter(s) of the detection algorithm to be used for the inspection recipe without performing an additional scan of the wafer subsequent to the scan.

20 Claims, 1 Drawing Sheet

U.S. PATENT DOCUMENTS

| | | | |
|---|---|---|---|
| 6,996,492 B1 * | 2/2006 | Testoni | 702/134 |
| 7,065,239 B2 * | 6/2006 | Maayah et al. | 382/145 |
| 7,440,086 B2 * | 10/2008 | Borowicz et al. | 356/72 |
| 7,587,704 B2 * | 9/2009 | Ye et al. | 716/51 |
| 2007/0061772 A1 * | 3/2007 | Ye et al. | 716/21 |
| 2007/0061773 A1 * | 3/2007 | Ye et al. | 716/21 |
| 2007/0067134 A1 * | 3/2007 | Borowicz et al. | 702/127 |
| 2009/0080759 A1 * | 3/2009 | Bhaskar et al. | 382/141 |
| 2009/0242760 A1 * | 10/2009 | Miyamoto et al. | 250/307 |
| 2009/0284733 A1 * | 11/2009 | Wallingford et al. | 356/73 |

FOREIGN PATENT DOCUMENTS

| | | |
|---|---|---|
| JP | 2004177139 A * | 6/2004 |
| JP | 2006-017744 | 1/2006 |
| JP | 2008-014650 | 1/2008 |
| KR | 10-2006-0128277 | 12/2006 |

OTHER PUBLICATIONS

U.S. Appl. No. 11/859,342 (Chen et al.) entitled Computer-Implemented Methods, Carrier Media, and Systems for Creating a Defect Sample for Use in Selecting One or More Parameters of an Inspection Recipe filed Sep. 21, 2007.

International Search Report and Written Opinion for PCT/US2009/045127, mailed Nov. 20, 2009.

International Preliminary Report on Patentability for PCT/US2009/045127 mailed Nov. 30, 2010.

* cited by examiner

METHODS AND SYSTEMS FOR GENERATING INFORMATION TO BE USED FOR SELECTING VALUES FOR ONE OR MORE PARAMETERS OF A DETECTION ALGORITHM

BACKGROUND OF THE INVENTION

1. Field of the Invention

This invention generally relates to methods and systems for generating information to be used for selecting values for one or more parameters of a detection algorithm. Certain embodiments relate to generating sufficient information for selecting values for one or more parameters of a detection algorithm to be used for an inspection recipe from results of a scan of a wafer performed without user intervention and without performing an additional scan of the wafer subsequent to the scan.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices. Accordingly, much work in the inspection field has been devoted to designing inspection systems that can detect defects having sizes that were previously negligible.

Many different types of inspection systems have adjustable output acquisition (e.g., data, signal, and/or image acquisition) and sensitivity (or defect detection) parameters such that different parameters can be used to detect different defects or avoid sources of unwanted (nuisance) events. Although an inspection system that has adjustable output acquisition and sensitivity parameters presents significant advantages to a semiconductor device manufacturer, these inspection systems are essentially useless if the incorrect output acquisition and sensitivity parameters are used for an inspection process. In addition, since the defects, process conditions, and noise on wafers may vary dramatically (and since the characteristics of the wafers themselves may vary dramatically), the best output acquisition and sensitivity parameters for detecting the defects on a particular wafer may be difficult, if not impossible, to predict. Therefore, although using the correct output acquisition and sensitivity parameters will have a dramatic effect on the results of inspection, it is conceivable that many inspection processes are currently being performed with incorrect or non-optimized output acquisition and sensitivity parameters.

An optimal inspection recipe for a semiconductor layer should detect as many defects of interest (DOI) as possible while maintaining a substantially low nuisance rate. Optimizing an inspection recipe generally involves tuning the parameters used in the recipe until the optimal result is achieved. The set of parameters to be tuned thus depends on the detection algorithm used. In the case of bright field (BF) inspection systems commercially available from KLA-Tencor, San Jose, Calif., the detection algorithms may be auto-thresholding (AT), segmented auto-thresholding (SAT) or multiple die auto-thresholding (MDAT), and the inspection parameters may be segment breaks and thresholds. In the case of dark field (DF) inspection systems commercially available from KLA-Tencor, the detection algorithms may be FAST and HLAT algorithms.

One best known method for recipe optimization is to run a substantially "hot" inspection thereby increasing the likelihood of detecting DOI but at the expense of substantially high nuisance rates. The user then takes this hot lot and the wafer to a scanning electron microscope (SEM) for review. The user reviews the defects using the SEM and classifies the defects as real, nuisance, or DOI. Once enough of each type of defect is classified, the user attempts to set the correct segment breaks and threshold values in order to create a recipe that will detect enough of the DOI and have as few as possible of the nuisance defects detected. The more defects that are classified, the better the recipe can be. The user may then re-inspect the wafer using the new recipe and use the SEM to review the defects detected on the wafer using the new recipe. In this manner, re-inspection and defect review may be performed in an iterative manner until the user determines that satisfactory defect detection can be achieved by the recipe based on defect review results.

One problem with such methods is that it takes significant time to SEM review a single defect. In addition, the need for multiple trips between the inspection system and the SEM adds significant time to the recipe setup. The user would ideally like to review the smallest number of defects possible that would still produce an accurate recipe and be able to do this in one trip to the SEM.

Accordingly, it would be advantageous to develop methods and/or systems for generating sufficient information for selecting values for one or more parameters of a detection algorithm to be used for an inspection recipe from results of a scan of a wafer performed without user intervention and without performing an additional scan of the wafer subsequent to the scan.

SUMMARY OF THE INVENTION

The following description of various embodiments of methods, computer-readable media, and systems is not to be construed in any way as limiting the subject matter of the appended claims.

One embodiment relates to a method for generating information to be used for selecting values for one or more parameters of a detection algorithm. The method includes performing a scan of an area of a wafer using an inspection system and default values for one or more parameters of a detection algorithm to detect defects on the wafer. The area of the wafer includes an entire area of the wafer that will be scanned using an inspection recipe. The scan is performed without user intervention. The method also includes selecting a portion of the defects from results of the scan based on a predetermined maximum number of total defects to be used for selecting values for the one or more parameters of the detection algorithm. In addition, the method includes storing information for the portion of the defects. The information includes values for the one or more parameters of the detection algorithm determined for the defects in the portion. The information can be used to select the values for the one or more parameters of the detection algorithm to be used for the inspection recipe without performing an additional scan of the wafer subsequent to the scan.

In one embodiment, prior to performing the scan, the method includes performing an initial scan of the wafer using the inspection system and default values for the one or more parameters of the detection algorithm and determining one or more parameters of selecting the portion of the defects based on results of the initial scan. In one such embodiment, the initial scan and determining the one or more parameters of selecting the portion of the defects are performed without user intervention. In another such embodiment, the initial scan and the scan are performed sequentially without input from a user between the initial scan and the scan.

In one embodiment, the method includes generating a multi-dimensional histogram for values for two or more of the parameters of the detection algorithm determined for defects detected during an initial scan performed prior to performing the scan and determining one or more parameters to be used for selecting the portion of the defects based on the multi-dimensional histogram, total number of the defects detected by the initial scan, the predetermined maximum number of the total defects, the entire area of the wafer that will be scanned using the inspection recipe, and an area of the wafer scanned during the initial scan. In one such embodiment, the values for the two or more of the parameters of the detection algorithm determined for the defects detected during the initial scan include values for threshold offset and median reference intensity, and information about the defects detected during the initial scan other than the multi-dimensional histogram and the total number of the defects detected by the initial scan is not saved.

In some embodiments, performing the scan without the user intervention includes performing the scan without input from a user for the default values for the one or more parameters of the detection algorithm and without input from the user for any other one or more parameters of the inspection recipe. In another embodiment, the default values for the one or more parameters of the detection algorithm used for the scan include a default value for a threshold applied to output generated by the scan to detect the defects on the wafer. In one such embodiment, the default value for the threshold is at or below a noise floor of the output generated by the scan.

In one embodiment, selecting the portion of the defects includes selecting the defects having larger values for the one or more parameters of the detection algorithm than other defects. In another embodiment, selecting the portion of the defects includes selecting the same number of defects for a substantial portion of bins in a multi-dimensional histogram for the values for two or more of the parameters of the detection algorithm. In an additional embodiment, the one or more parameters of the detection algorithm include frames, segments, and regions, and the predetermined maximum number of total defects includes only one defect per frame per segment per region.

In one embodiment, the values for the one or more parameters that can be selected without requiring the additional scan of the wafer include values for segment breaks. In another embodiment, the values for the one or more parameters that can be selected without requiring the additional scan of the wafer include values for segment breaks and values for thresholds for segments, and the values for the segment breaks and the thresholds can be selected simultaneously.

In some embodiments, the values for the one or more parameters of the detection algorithm determined for the defects include triggered threshold offset and median intensity value. In another embodiment, the information includes a multi-dimensional histogram for the values for two or more of the parameters of the detection algorithm determined for the defects in the portion. In an additional embodiment, the information includes patch images for the defects in the portion acquired by the inspection system during the scan. In a further embodiment, the information can be used to select the values for all parameters of the detection algorithm without performing the additional scan of the wafer subsequent to the scan.

In one embodiment, the inspection recipe includes an inspection recipe for bright field (BF) inspection of the wafer. In another embodiment, the inspection recipe includes an inspection recipe for dark field (DF) inspection of the wafer.

Each of the steps of each of the embodiments of the method described above may be performed as described further herein. In addition, each of the embodiments of the method described above may include any other step(s) of any other method(s) described herein. Furthermore, each of the embodiments of the method described above may be performed by any of the systems described herein.

Another embodiment relates to a computer-readable medium that includes program instructions executable on a computer system for performing a method for generating information to be used for selecting values for one or more parameters of a detection algorithm. The method includes performing a scan of an area of a wafer using an inspection system and default values for one or more parameters of a detection algorithm to detect defects on the wafer. The area of the wafer includes an entire area of the wafer that will be scanned using an inspection recipe. The scan is performed without user intervention. The method also includes selecting a portion of the defects from results of the scan based on a predetermined maximum number of total defects to be used for selecting values for the one or more parameters of the detection algorithm. In addition, the method includes storing information for the portion of the defects. The information includes values for the one or more parameters of the detection algorithm determined for the defects in the portion. The information can be used to select the values for the one or more parameters of the detection algorithm to be used for the inspection recipe without performing an additional scan of the wafer subsequent to the scan.

The computer-readable medium described above may be further configured as described herein. The steps of the method may be performed as described further herein. In addition, the method for which the program instructions are executable may include any other step(s) of any other method(s) described herein.

An additional embodiment relates to a system configured to generate information to be used for selecting values for one or more parameters of a detection algorithm. The system includes an inspection system configured to perform a scan of an area of a wafer using default values for one or more parameters of a detection algorithm to detect defects on the wafer. The area of the wafer includes an entire area of the wafer that will be scanned using an inspection recipe. The scan is performed without user intervention. The system also includes a computer system configured to select a portion of the defects from results of the scan based on a predetermined maximum number of total defects to be used for selecting values for the one or more parameters of the detection algorithm. The computer system is also configured to store information for the portion of the defects. The information includes values for the one or more parameters of the detection algorithm determined for the defects in the portion. The information can be used to select the values for the one or more parameters of the detection algorithm to be used for the inspection recipe without performing an additional scan of the wafer subsequent to the To scan. The system may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the embodiments may be used for generating information to be used for selecting values for one or more parameters of a detection algorithm to be used for inspection of another specimen such as a reticle, which may also be commonly referred to as a mask or a photomask. Many different types of reticles are known in the art, and the terms "reticle," "mask," and "photomask" as used herein are intended to encompass all types of reticles known in the art.

The term "detection algorithm" as used herein generally refers to an algorithm that can be applied to output acquired by scanning a wafer to detect defects on the wafer.

For inspection tools and systems such as those commercially available from KLA-Tencor, San Jose, Calif., and other inspection tool manufacturers, customers and application engineers spend a tremendous amount of time in inspection recipe set up. Reducing the recipe set up cycle and improving the tool to ease the recipe set up process are extremely important in the competitive market. Setting up a detection algorithm recipe is commonly an iterative process. For example, a user would scan a wafer to identify an initial recipe and then scan the wafer a second time using the identified initial recipe to collect a "hot" scan result to be used for recipe set up.

Adding to the complexity, often a detection algorithm recipe has multiple segments with each segment having its own recipe parameters. "Segments" can be generally defined as different portions of image intensity values across an entire range of possible image intensity values. In one such illustrative and non-limiting example, if the entire range of image intensity values is from 0 to 255, a first segment may include image intensity values from 0 to 100 and a second segment may include image intensity values from 101 to 255. In this manner, the first segment corresponds to darker areas in the image, and the second segment corresponds to brighter areas in the image. Different recipe parameters such as thresholds may be set for each segment so that different thresholds can be used to detect defects in different segments.

In order to move segment breaks, wafer rescanning is required to collect new data for recipe tuning for the newly selected segment breaks. In this manner, unlike the one step approach provided by the embodiments described further herein, other methods are iterative processes and require human intervention in order to collect enough data for recipe set up especially when a recipe has multiple segments and changing segment breaks is desirable.

Other methods and systems for generating information that can be used to select values for one or more parameters of a detection algorithm, therefore have a number of disadvantages. For example, a relatively rough estimate of frame defectivity is determined during an initial scan, which roughly measures a triggered threshold offset for each frame. Frame defectivity only records the smallest threshold offset that, when applied to output for the frame acquired by scanning, results in detection of a defect in the frame without information about how many defects are detected for a particular threshold offset. In other words, frame defectivity does not capture or reflect information about real defects in the frame such as the location of the defect(s) in the frame, how many defect(s) are in the frame, and the like. Therefore, frame defectivity is a poor prediction of the defectivity that can be expected on the wafer. As a result, a recipe identified from the initial scan for a second scan is often not accurate enough and causes the second scan results to be too "hot" or too "cold" for recipe set up purposes. In addition, one-dimensional (1D) accumulative histogram data is collected for each segment separately, which causes the requirement of rescanning when segment break tuning is required. For example, when this approach is used to tune segments, changing the segments by changing the segment breaks will cause some defects to be in different segments. However, since the 1D histogram data is collected for each segment separately, the wafer has to be rescanned such that the histogram data can be recollected for the newly defined segments. Furthermore, segment breaks need to be pre-specified before the initial scan. In this manner, the second scan and final tuned detection algorithm recipe have to use the same segment breaks. Moreover, human intervention is required during the wafer scan process.

The embodiments described herein generally relate to a one step tuning scan (OSTS) for detection algorithm recipe set up and segment break tuning. For example, one embodiment relates to a method for generating information to be used for selecting values for one or more parameters of a detection algorithm. The embodiments described herein provide a one step approach for collecting enough defects with associated defect information for offline recipe set up. For example, without the need of user intervention the embodiments can automatically collect a pre-specified number of defects (e.g., that an inspection system can handle) that can be used by the user to set up the recipe. In this manner, users do not need to worry about any initial recipe parameters or segment breaks. Instead, the embodiments described herein automatically collect enough defect information to allow users to tune segment breaks and set up the recipe for each segment without the need of rescanning.

As described further herein, the values for the one or more parameters of the detection algorithm may be selected for use in an inspection recipe. A "recipe" is generally defined as a set of instructions that can be used by a system such as an inspection system to perform a process such as an inspection process. The methods described herein are not limited in the types of detection algorithms (or inspection systems and inspection recipes that execute such detection algorithms) for which values for one or more parameters can be selected using the information generated as described herein. For example, in one embodiment, the inspection recipe includes an inspection recipe for bright field (BF) inspection of the wafer. In this manner, the inspection system may include a BF inspection system. The BF inspection system may be configured as described further herein. In another embodiment, the inspection recipe includes an inspection recipe for dark field (DF) inspection of the wafer. In this manner, the inspection system may include a DF inspection system. The DF inspection system may have any suitable configuration known in the art. The inspection system may also be configured for BF and DF inspection. In addition, the inspection system may be configured for inspection of patterned wafers and/or unpatterned wafers.

The detection algorithm may include any suitable detection algorithm known in the art. In one embodiment, the detection algorithm is an auto-thresholding (AT) algorithm. In an additional embodiment, the detection algorithm is a segmented auto-thresholding (SAT) algorithm. In another embodiment, the detection algorithm is a multiple die auto-thresholding (MDAT) algorithm. Such detection algorithms may be particularly suitable for BF inspection. However, the detection algorithm may be a detection algorithm that is suitable for DF inspection. For example, in one embodiment, the detection algorithm is a FAST algorithm or an HLAT algorithm.

Information generated according to embodiments described herein may also be used to optimize one or more parameters of a detection algorithm included in an inspection recipe. In addition, information generated according to embodiments described herein may be used to optimize any type of inspection recipe (e.g., a DF or BF inspection recipe) that includes any type of detection algorithm (e.g., a FAST algorithm, an HLAT algorithm, an AT algorithm, a SAT algorithm, a MDAT algorithm, etc.). For example, OSTS may be used for recipe tuning for detection algorithms such as the MDAT algorithm and others. In addition, the methods described herein can be extended to support different algorithms that use the MDAT algorithm as the basic detection engine.

In one embodiment, prior to performing the scan described further herein (also referred to as "the final scan") of a wafer, the method includes performing an initial scan of the wafer using the inspection system and default values for the one or more parameters of the detection algorithm and determining one or more parameters of the step of selecting a portion of the defects described herein based on results of the initial scan. For example, the initial scan may use threshold offsets of 0 for each segment and a default number of segments to detect defects. The number of defects detected by the initial scan may be limited to a user-configurable number of peak defects (by default one defect) per frame per segment per region for the BF MDAT algorithm. In a similar manner, for a DF algorithm, the OSTS initial scan may use default threshold values for HLAT and FAST algorithms and default number of segments to detect defects up to a user-configurable number of peak defects (by default 2 defects) per segment per region. The term "peak defects" refers to defects detected with relatively larger threshold parameters. For example, peak defects may include defects for which stronger defect signals are detected. A "region" can be generally defined as a region on a wafer that includes a particular type of pattern (e.g., a region in which an array pattern is formed, a region in which a random pattern is formed, a region in which a different array pattern is formed, and the like) having particular pattern characteristics (e.g., pitch, period, and the like). The regions in the algorithm may be user-defined or defined in any other suitable manner.

The area of the wafer that is scanned in the initial scan may be different than the area that is scanned in the final scan in that the area of the wafer that is scanned in the initial scan may be less than the area of the wafer that is scanned in the final scan. For example, the area that is scanned in the initial scan may be only the area on the wafer in which the center die row is located or only a percentage of the wafer area that will be scanned in the inspection recipe In addition, the initial scan may cover a small percentage of the same area of the wafer covered by the final scan. For example, the initial scan may include scanning a different area on the wafer or the same area as the final scan but with less percentage coverage in the initial scan compared to the final scan. Furthermore, the area of the wafer that is scanned in the initial scan may be a subset of the area that is scanned in the final scan.

The initial scan may be performed to estimate the defectivity of the entire area of the wafer that will be scanned in the final scan. In other words, results of the initial scan may be used to estimate or predict how many defects are on the whole wafer. For example, the area of the wafer scanned during the initial scan may include the center die row. The center die row may include 10 dies, and the entire wafer may include 100 dies. If 100 defects are detected by the initial scan of the center die row, then it can be estimated that a scan of all 100 dies will result in detection of about 1000 defects. In this manner, based on the defect count for the center die row, the method may include projecting the defect count for the whole wafer proportionally based on the die sample plan for the inspection recipe.

If the number of defects estimated to be detected by the final scan is greater than that which can be handled by the computer system that will process the defects, one or more parameters of selecting a portion of defects from the results of the final scan may be selected based on the results of the initial scan. For example, if the number of defects estimated to be detected by the final scan is larger than the maximum number of defects that can be handled by the system, a selection strategy may be determined as described further herein such that the defects for which information is stored can be handled by the system while providing sufficient information (e.g., information for defects detected in backgrounds having different intensity values) for selecting the values for the one or more parameters of the detection algorithm.

In one embodiment, the initial scan and determining the one or more parameters of the selecting step are performed without user intervention. In another embodiment, the initial scan and the final scan are performed sequentially without input from a user between the initial scan and the final scan. For example, the two scans may be performed sequentially without input from a user as to the values of one or more parameters (thresholds) of the detection algorithm to be used for the initial and final scans. In addition, users may not even be aware of or have access to the results of the initial scan (e.g., center die row OSTS). In this manner, OSTS may include two scans that are performed sequentially without the need of user intervention. In addition, the two scans may be performed for each optical mode that will be used in the inspection recipe. In some such instances, users can run OSTS for different optics modes overnight if preferred.

The initial scan may use a threshold offset of 0 to detect defects and default segments as described above to create a two-dimensional (2D) histogram that reflects or indicates the wafer defectivity level. For example, in another embodiment, the method includes generating a multi-dimensional histogram for values for two or more of the parameters of the detection algorithm determined for defects detected during an initial scan performed prior to performing the final scan. In this manner, OSTS may include a wafer scan part that includes an initial scan that saves a 2D histogram. For example, BF detection algorithm parameters (or "features") that are determined for the defects detected during the initial scan may include triggered threshold offset, median intensity value, and others. A "triggered threshold offset" can be generally defined as the largest threshold offset that can detect a defect. In other words, the triggered threshold offset can be defined as the value of the threshold when a defect goes from detectable to undetectable. As such, the triggered threshold offset is just slightly less than the actual value for the defect. Therefore, the triggered threshold offset determined for a defect provides an indication of the actual detection value of the defect. The median intensity value is a parameter of the MDAT algorithm. For random defect detection, the MDAT algorithm creates a 2D histogram to detect a defect. For example, a reference pixel is subtracted from a test pixel at corresponding locations in a number of die on the wafer. In addition, a median intensity value is determined on a pixel to pixel basis for corresponding frames in a number of die on the wafer. The 2D histogram used for defect detection is then created by plotting the results of subtracting the reference pixel from the test pixel on the x axis of the histogram and the median intensity value on the y axis of the histogram. That 2D histogram is then used to detect defects. The median intensity value therefore gives an indication of the intensity of the background of the defect and therefore can be used as described further herein to help a user to determine values of one or more parameters (such as segment breaks) of the detection algorithm to be used for the inspection recipe.

For all peak defects, algorithm parameters such as triggered threshold offset and median intensity value saved for each peak defect may be used to form the 2D histogram. (Most defects only have one pair of triggered threshold offset and median intensity value. However, a relatively large defect may have up to four pairs with one from each segment.) In this manner, a 2D defect count histogram of threshold offset versus median reference intensity may be collected from a scan area on the wafer, which may be smaller so than the area scanned in the final scan, based on real scan data. The 2D histogram, therefore, contains relatively accurate information about how many defects are detected for each threshold offset versus median reference intensity. The noise floor can be observed from the 2D scatter histogram. The 2D histogram may be created for only a subset of the defects detected by the initial scan (e.g., 1 peak defect per frame per segment per region or 2 peak defects per segment per region). However, the 2D histogram may be created based on all defects detected by the initial scan. In this manner, the initial scan of OSTS may be performed without defect sampling to collect data on a partial wafer scan, for example, of one die row.

The values for two or more of the parameters of the detection algorithm determined for the defects detected during the initial scan may include values for any suitable parameters of any suitable detection algorithm and may, therefore, vary depending on the detection algorithm to be used in the inspection recipe. For example, as described above, the one or more parameters may include median intensity value and/or triggered threshold offset included in a detection algorithm such as AT, SAT, and MDAT. However, OSTS may collect DF algorithm-specific features for each defect. For example, the one or more parameters may include algorithm-related features of the defects such as defect difference intensity, FAST algorithm threshold, HLAT algorithm threshold, polarity, noise, absolute minimum (ABSMIN), or some combination thereof. Such parameters may be included in a detection algorithm used for DF inspection.

One such embodiment of the method also includes determining one or more parameters to be used for the selecting step described further herein (i.e., selecting a portion of the defects) based on the multi-dimensional histogram, total number of the defects detected by the initial scan, the predetermined maximum number of the total defects to be used for selecting the values for the one or more parameters of the detection algorithm, the entire area of the wafer that will be scanned using the inspection recipe, and an area of the wafer scanned during the initial scan. For example, based on the 2D histogram, a pre-specified final defect count, and the scan area ratio of the first and second scans, OSTS may automatically generate a "defect down sampling strategy" and a "defect down sampling algorithm" that can be used to perform the strategy. The defect down sampling algorithm may divide pixels in the 2D histogram or scatter plot into certain evenly distributed (32, for instance) bins along an axis for a parameter of the detection algorithm (e.g., the axis for the median intensity value). In this manner, at the end of the initial scan, based on the 2D histogram, the pre-specified final defect count, and inspection area ratio between the initial and final scans, an algorithm may automatically produce a defect down sampling recipe, which is an array of thresholds corresponding to a default number of bins (e.g., 32 bins) along the reference median intensity axis.

The defect down sampling algorithm may aim to preserve the same number of defects in each bin. For example, the defect down sampling strategy may be aimed at generating the predetermined maximum number of total defects that are evenly distributed along the reference median intensity axis. For bins with substantially few defects, the extra defect quota may be evenly redistributed to the rest of the bins. For example, if the defect down sampling strategy is to distribute 10,000 defects to each bin but there are only 1,000 detected defects for one bin, the 9,000 defects that cannot be distributed to that bin can be evenly redistributed across the other bins (e.g., the number of defects to be added to each bin can be determined by using a function such as 9,000/(number of bins−1)). Inside each bin, defects with larger triggered threshold offset values will be preserved.

In this manner, the defect down sampling recipe generation algorithm may use a 2D histogram generated during the initial scan, the predetermined maximum number of total defects, which may be defined in a configuration file, and the inspection area ratio between the initial and final scan to generate a defect down sampling algorithm that is aimed at generating an OSTS lot (i.e., a lot or population of defects from the final scan) that has a pre-specified number of defects substantially evenly distributed along the reference intensity background. Therefore, the information that is stored as described further herein and can be used to select the values for the one or more parameters of the detection algorithm to be used for the inspection recipe may advantageously include information about defects from all different backgrounds (i.e., backgrounds having different intensity values) thereby providing information for many different kinds of defects. The defect down sampling algorithm may be saved in a recipe that can be used for the subsequent whole wafer OSTS scan to keep defects in each bin above a certain threshold. In this manner, the defect down sampling algorithm may keep defects in each bin above a certain threshold and discard defects in each bin below the threshold.

Different defect down sampling strategies may be appropriate for different detection algorithms. For example, for a DF algorithm, a defect down sampling algorithm may use a defect count ratio for different regions to retain defects. In one such example, if region A has twice as many defects as region B for an initial scan, the final returned defects in region A may be double that selected from region B.

In one embodiment, the values for the two or more of the parameters of the detection algorithm determined for the defects detected during the initial scan include values for threshold offset and median reference intensity, and information about the defects detected during the initial scan other than the multi-dimensional histogram and the total number of the defects detected by the initial scan is not saved. For example, only peak defects may be collected to extract the defect threshold offset versus reference median intensity information. In addition, in the initial scan, only a 2D histogram of defect count for each median reference intensity versus threshold offset may be saved without information about the real defects. For example, OSTS may provide the function to save only the 2D histogram in the initial scan. Saving such information without information about the real defects eases the inspection system burden of handling a larger amount of defects during the initial scan. Furthermore, although the 2D histograms are described herein as histograms for threshold offset versus median intensity, the embodiments described herein can also be extended to support different 2D histogram axes other than threshold offset versus median intensity when other useful features of the detection algorithm are identified.

The method includes performing a scan of an area of a wafer using an inspection system and default values for one or more parameters of a detection algorithm to detect defects on the wafer. This scan is also referred to herein as the "final scan" in that an initial scan may be performed before this scan, but no additional scan will be performed after this scan for the purpose of generating information to be used for selecting values for one or more parameters of the detection algorithm. The wafer scan part of OSTS, therefore, includes a final scan. The inspection system used to perform the final scan may be any of the inspection systems described herein.

In addition, preferably, the same inspection system is used to perform the initial and final scans. The area of the wafer scanned in the final scan includes an entire area of the wafer that will be scanned using an inspection recipe. For example, the area of the wafer may include the entire area of a surface of the wafer if the entire area of the surface of the wafer will be scanned using the inspection recipe. However, if some areas of the wafer will not be scanned using the inspection recipe, those areas may also not be scanned during the final scan.

The scan is performed without user intervention. For example, the method provides a one step approach for collecting enough data for recipe segment break tuning and recipe set up without user intervention. In one embodiment, performing the scan without user intervention includes performing the scan without input from a user for the default values for the one or more parameters of the detection algorithm and without input from the user for any other one or more parameters of the inspection recipe. In this manner, users do not need to worry about the initial recipe set up or segment breaks.

The detection algorithm used for the final scan is preferably the same detection algorithm used for the initial scan. In one embodiment, the default values for the one or more parameters of the detection algorithm used for the scan include a default value for a threshold applied to output generated by the scan to detect the defects on the wafer, and the default value for the threshold is at or below a noise floor of the output generated by the scan. In this manner, OSTS "digs" into the noise floor and does not require a threshold guess by a user. Instead, a default hot threshold is used to detect all defects. The default values used for the final scan may be automatically generated values, which may be generated based on the initial scan results, total number of the final defect count, and the scanned area ratio between the initial and final scans. For example, the final scan may use non-zero auto-generated threshold offsets. The default values for the one or more parameters of the detection algorithm used for the scan may also include any other default values described herein (e.g., a default number of segments). In addition, the same default values for some of the one or more parameters of the detection algorithm may be used for the initial and final scans. For example, default segment breaks for data collection may be the same default values (or the only same default values) for the initial and final scans. In this manner, the default values for the one or more parameters of the detection algorithm used for the final scan may be predetermined or may vary depending on the results of the initial scan. However, the default values for the one or more parameters of the detection algorithm used for the final scan, whether they are predetermined or variable, are advantageously not user-selected values.

The OSTS final scan uses a "real" inspection scan method to detect the defects on the wafer. For example, during the OSTS final scan, scanning the wafer is performed in the same manner that the wafer will be scanned during a real inspection, and applying a detection algorithm to output generated by the scan to detect the defects is performed in the same manner that the detection algorithm will be applied to the output during a real inspection scan. In addition, the defects may be detected during the OSTS final scan using a double detection method such that the defects that are detected are real or actual defects and other inspection-like results may be produced by the OSTS final scan (e.g., defect patch images) and stored as described further herein. In this manner, the information collected by the final scan is advantageously real detection information for real or actual defects, which advantageously provides real detection information for selecting values for one or more parameters of the detection algorithm to be used for the inspection recipe.

The method also includes selecting a portion of the defects from results of the scan based on a predetermined maximum number of total defects to be used for selecting values for the one or more parameters of the detection algorithm. For example, to ensure that the defect count for the "whole wafer" scan is below a certain limit, defect down sampling may be applied for some wafer layers. In this manner, defect down sampling may be performed to control the defect count. As described above, a defect down sampling strategy may be generated after the initial scan. From initial scan results that cover a smaller area on the wafer than the final scan, the total defect count on the whole wafer may be projected based on the wafer sampling plan. If the projected defect count on the whole wafer exceeds the limit, the defect down sampling may be applied to the results of the subsequent whole wafer scan. In this manner, the wafer scan part of OSTS includes a final scan, which may collect a pre-specified number of defects. The predetermined maximum number of total defects may be a default pre-specified defect count defined in a configuration file. A user can either choose the default number or modify the default number. In this manner, the selecting step may include defect down sampling, and is referred to herein as the "defect down sampling step." The OSTS final scan may invoke the defect down sampling strategy automatically to generate the final lot result.

In one embodiment, selecting the portion of the defects includes selecting the defects having larger values for the one or more parameters of the detection algorithm than other defects. For example, although a default hot threshold may be used to detect all defects as described above, only peak defects per frame per segment per region may be selected. In this manner, some defects detected near the noise floor may be eliminated while defects with relatively large defect signals may be retained. In one embodiment, the one or more parameters of the detection algorithm include frames, segments, and regions, and the predetermined maximum number of total defects includes only one defect per frame per segment per region. The regions used to separate the defects may be defined in any suitable manner (e.g., different regions may correspond to different portions of a design printed (or to be printed) on the wafer), and the defects may be separated based on region using any suitable method, algorithm, system, or technique.

In another embodiment, selecting the portion of the defects includes selecting the same number of defects for a substantial portion of bins in a multi-dimensional histogram for the values for two or more of the parameters of the detection algorithm. Selecting the portion of the defects in this manner may be performed using the defect down sampling strategies described further herein. For example, OSTS may be aimed to generate a lot that has the predetermined maximum number of total defects substantially evenly distributed across different reference intensity backgrounds. In one such example, based on the 2D histogram, a pre-specified final defect count for the final whole wafer scan, and the inspected area ratio, the method may automatically collect a substantially even amount of defects for different reference intensity backgrounds. The substantial portion of the bins in the multi-dimensional histogram for which the same number of defects is selected may include all of the bins except those with substantially few defects, which causes the defect quota for those bins to be redistributed evenly to other bins. Defects may be collected substantially evenly across the entire reference intensity range by default. However, users can also choose to collect more defects in certain intensity ranges than others. In this manner, OSTS can be extended to allow users to specify the desired defect distribution along the median intensity axis.

The method further includes storing information for the portion of the defects. The information may be stored in a storage medium. The information may include any of the information described herein and may be stored in any manner known in the art. The storage medium may include any suitable storage medium known in the art. After the information has been stored, the information can be accessed in the storage medium and used as described herein, formatted for display to a user, used by another software module, method, or system, etc. For example, the information may be stored such that the user can access and use the information to select values for one or more parameters of the detection algorithm as described further herein (e.g., by reviewing a sample of the defects on a defect review tool (e.g., a scanning electron microscope (SEM)) in order to classify the defects and determine appropriate values for one or more parameters of the detection algorithm to be used for the inspection recipe). Furthermore, the information may be stored "permanently," "semi-permanently," temporarily, or for some period of time. For example, the storage medium may be random access memory (RAM), and the results may not necessarily persist indefinitely in the storage medium.

In this manner, the method may not include storing information for all defects detected by the final scan. For example, as described above, although a default hot threshold may be used to detect all defects, only information for peak defects per frame per segment per region may be stored. The information includes values for the one or more parameters of the detection algorithm determined for the defects in the portion. For example, as described above, OSTS uses the same method as a real inspection scan to detect defects, but only peak defects as well as values for algorithm feature(s) for each peak defect may be stored. In one embodiment, the values for the one or more parameters of the detection algorithm determined for the defects include triggered threshold offset and median intensity value. In this manner, OSTS may collect algorithm features including threshold offset and multiple die/cell features, which can be used to form a multiple dimension scatter plot as described herein.

The information can be used to select the values for the one or more parameters of the detection algorithm to be used for the inspection recipe without performing an additional scan of the wafer subsequent to the scan. For example, a user may load the lot result to an OSTS sensitivity tuner software module either online or offline to tune the detection algorithm recipe. The OSTS lot generated as described herein may be loaded to the OSTS sensitivity tuner to tune the segment breaks and any other parameter(s) of the detection algorithm such as threshold offsets. For example, as described above, OSTS collects algorithm features such as triggered threshold offset and multiple die/cell features to form a multiple dimension scatter plot that allows users to tune segment breaks and threshold parameters on top of the scatter plot. In addition, OSTS can be extended to support continuously threshold offset setting along the median intensity axis. For example, a continuous threshold offset curve can be drawn (e.g., by a user) on the 2D scatter plot as recipe threshold parameters. In this manner, the detection algorithm recipe may be tuned continuously in 2D space.

In one embodiment, the values for the one or more parameters that can be selected without requiring the additional scan of the wafer include values for segment breaks. In this manner, the embodiments described herein allow users to tune segment breaks without the need of wafer rescanning. Therefore, OSTS is a single step approach for recipe tuning. In contrast, previous approaches require human intervention and multiple steps including Initial Threshold Finder (ITF) and Sensitivity Tuner (ST) scans. Each pair of ITF and ST scans can only support threshold tuning for fixed segment breaks. In other words, changing segment breaks requires new ITF and ST scans. Therefore, the previous two scan approaches do not support segment break tuning. However, users can tune segment breaks using OSTS. For example, as described further herein, the information that is stored for the selected portion of the defects includes values for the one or more parameters of the detection algorithm determined for the defects in the portion. In addition, as described further herein, the values for the one or more parameters of the detection algorithm determined for the defects in the portion may include median reference intensity. In this manner, when segment tuning involves changing segment breaks, the stored median reference intensity values allow the embodiments described herein to determine which defects move from one segment into another due to the altered segment breaks. As such, when segment breaks are changed, the data for the segments defined by the new segment breaks can be re-determined from stored information thereby eliminating the need to reacquire that data by scanning the wafer.

In another embodiment, the values for the one or more parameters that can be selected without requiring the additional scan of the wafer include values for segment breaks and values for thresholds for segments, and the values for the segment breaks and the thresholds can be selected simultaneously. In this manner, the stored information can be used for simultaneous segment breaks and threshold tuning. As such, the embodiments described herein provide the functionality of allowing simultaneous segment break tuning and threshold tuning for each segment. In addition, since, as described further herein, the information can be generated and stored without user intervention, the embodiments described herein support simultaneous segment breaks and threshold tuning without the need of user intervention. For instance, previously, users have to decide segment breaks first and then scan the wafer to collect data to tune threshold parameters for the predefined segment breaks. If the users want to change segment breaks, they have to rescan the wafer using the changed segment breaks to tune threshold parameters for the changed segment breaks. Therefore, the embodiments described herein provide tremendous value to the user in terms of setting up recipes quickly and achieving higher sensitivity.

In some embodiments, the information includes a multi-dimensional histogram for the values for two or more of the parameters of the detection algorithm determined for defects in the portion. For example, a user interface may be configured and used to display a 2D histogram such as that described above and to allow a user to add/delete/move segment breaks and tune the recipe. In one such example, from the OSTS sensitivity tuner, the user can view the 2D histogram, add/delete/move segment breaks on the 2D histogram, and tune (or set) threshold offsets and any other parameter(s) for each segment on the 2D histogram. In a similar manner, a 2D scatter plot showing values for triggered threshold offset on the x axis for the defects in the portion versus values for median intensity on the y axis for the defects in the portion may be displayed on a user interface and used by the user to set segment breaks and parameter(s) for each segment. For example, triggered threshold offset and median intensity values for all peak defects may be used to form the 2D scatter plot described above. Different defects may be displayed in the 2D scatter plot in different manners. For example, killer defects, nuisances, and defects not of interest to the user may be displayed in different manners (e.g., with different formatting such as color). The noise floor can also be observed from the 2D scatter plot. In this manner, users can add/delete/move segment breaks as well as define a threshold for each segment on top of the 2D scatter plot to tune the recipe.

An OSTS sensitivity tuning algorithm may also read in the algorithm features for the portion of the defects (e.g., by accessing the information stored as described herein) and use the algorithm features to predict the detection results for a user-selected detection algorithm recipe. For example, based on the user-selected segment breaks and threshold offset for each segment, the OSTS segment tuner may determine the number of defects detected in each segment using the defect information collected in the final OSTS scan. As a user applies the selected recipe, a wafer map may be updated to reflect the prediction of the recipe. For example, from the OSTS sensitivity tuner, users can apply the tuned recipe, and the wafer map may be updated to reflect the detection of the current recipe. In this manner, the wafer map may be updated after users apply the tuned recipe to display the defects detected by the current recipe. Therefore, users can easily observe how the changes to the values for the one or more parameters of the detection algorithm for use in the inspection recipe will alter the defect population that will be detected by the inspection recipe. In this manner, the user may iteratively apply different values for the segment breaks and parameter(s) for the segments. For example, once users "apply" the selected segment breaks and threshold offsets, the users may observe the changes in the wafer map and then re-tune the threshold offsets based on the changed wafer map until the wafer map reflects the defect detection results desired by the users. The wafer map may include any suitable wafer map and may be created and updated in any suitable manner. In addition, any other type of feedback may be used to provide the users with an indication of how their changes to the values for the one or more parameters of the detection algorithm will alter the defects that will be detected by the inspection recipe. For example, the feedback may include a table or listing which indicates the number of defects that will be detected per defect classification code or per location or region in the die with any other additional information such as defect patch images.

Users may also draw a continuous curve surrounding the noise floor as a detection algorithm recipe parameter. For example, the noise floor can be observed in the 2D histogram created as described above. The 2D histogram can be displayed in a user interface, and a user can use any suitable input device or method to draw a curve separating the noise from other areas of the 2D histogram. The area in the 2D histogram corresponding to the noise therefore represents the noise floor that may be present in output acquired for a wafer using the inspection recipe, and information about the noise floor can be used in various ways. Users may also review the selected portion of the defects using a defect review tool such as a SEM to help in selecting the final detection algorithm recipe. In some such instances, a user may choose to SEM review defects using a "smart sampling" algorithm or method such as one of those described in commonly owned U.S. patent application Ser. No. 11/859,342 by Chen et al. filed Sep. 21, 2007, which is incorporated by reference as if fully set forth herein. The embodiments described herein may include any step(s) of any method(s) described in this patent application. Users may choose to save the final tuned recipe from the OSTS sensitivity tuner. In this manner, a user can save the tuned recipe to complete the OSTS recipe tuning.

In another embodiment, the information includes patch images for the defects in the portion acquired by the inspection system during the scan. For example, OSTS provides defect patch images (or "defect patches") that users may use to classify defects to help in recipe tuning. With the help of defect patches and defect classification, users can complete the recipe set up with OSTS. In addition, with enough classified defects, the algorithm can automatically generate segment breaks and a threshold offset for each segment. Similarly, using classified defects (e.g., classified real defects and nuisances), the method may include automatically generating the continuous threshold offset curve on the 2D scatter plot as detection algorithm recipe threshold parameters. The information may also include patch images in combination with any other information described herein. For example, from the OSTS sensitivity tuner, the user can view the defect patch images and 2D histogram to help in selecting segment breaks and threshold offsets.

In an additional embodiment, the information can be used to select the values for all parameters of the detection algorithm without performing the additional scan of the wafer subsequent to the scan. For example, OSTS can be extended to support tuning other parameters such as threshold max. In one such example, the threshold max can be set automatically to the value of the threshold offset plus an integer (e.g., 64). In this manner, the information can be used to select the values for the parameters described herein and any other parameters of a detection algorithm such as threshold max.

As described above, the number of the defects included in the selected portion of the defects may be limited to some predetermined maximum number, which may be determined based on the storage capacity of the system and/or the information processing capacity of the system. However, the system used to store and process the information may be configured as described in commonly owned U.S. patent application Ser. No. 60/974,030 by Bhaskar et al. filed Sep. 20, 2007, which is incorporated by reference as if fully set forth herein. The systems and methods described in this patent application are capable of storing and processing massive amounts of information for wafers. Those systems and methods may be adapted to store and process the information described herein for all of the defects detected on the wafer by the scan (the final scan). After such information has been stored, a portion of the defects may be selected, and only the information for that portion of the defects may be used to select the values for the one or more parameters of the detection algorithm to be used for the inspection recipe. However, after such information has been stored, the information for all of the defects may be used to select the values for the one or more parameters of the detection algorithm to be used for the inspection recipe. In this manner, the embodiments described herein may or may not include the initial scan, creating a defect down sampling strategy, and defect down sampling of the defects detected by the final scan. In addition, or alternatively, the information for all of the defects may be used to perform one or more other defect-related functions, including any of those described in the above-referenced patent application.

Each of the embodiments of the method described above may include any other step(s) of any other method(s) described herein. Furthermore, each of the embodiments of the method described above may be performed by any of the systems described herein.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
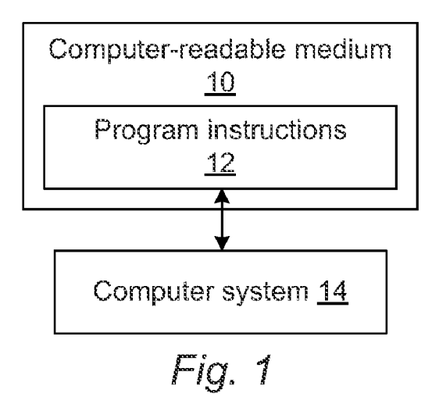
FIG. 1 is a block diagram illustrating one embodiment of a computer-readable medium that includes program instructions executable on a computer system for performing one or more of the method embodiments described herein.

Another embodiment relates to a computer-readable medium that includes program instructions executable on a computer system for performing a method (i.e., a computer-implemented method) for generating information to be used for selecting values for one or more parameters of a detection algorithm. One such embodiment is shown in FIG. 1. In particular, as shown in FIG. 1, computer-readable medium 10 includes program instructions 12 executable on computer system 14.

The method includes performing a scan of an area of a wafer using an inspection system and default values for one or more parameters of a detection algorithm to detect defects on the wafer. The scan may be performed according to any of the embodiments described herein. The inspection system may be configured as described herein. The default values for the one or more parameters may include any of the default values described herein. The one or more parameters of the detection algorithm may include any of the one or more parameters described herein. The detection algorithm may include any of the detection algorithms described herein or any other suitable detection algorithm. The area of the wafer includes an entire area of the wafer that will be scanned using an inspection recipe. The inspection recipe may include any of the inspection recipes described herein. The scan is performed without user intervention. The scan may be performed without user intervention according to any of the embodiments described herein.

The method also includes selecting a portion of the defects from results of the scan based on a predetermined maximum number of total defects to be used for selecting values for the one or more parameters of the detection algorithm. Selecting the portion of the defects may be performed according to any of the embodiments described herein. The results of the scan used to select the portion of the defects may include any of the results described herein.

The method further includes storing information for the portion of the defects. Storing the information for the portion of the defects may be performed according to any of the embodiments described herein. The information includes values for the one or more parameters of the detection algorithm determined for the defects in the portion, which may include any of such values described herein. The stored information may also include any other information described herein. The information can be used to select the values for the one or more parameters of the detection algorithm to be used for the inspection recipe without performing an additional scan of the wafer subsequent to the scan. The information can be used to select the values for the parameter(s) of the detection algorithm according to any of the embodiments described herein. The method for which the program instructions are executable may include any other step(s) described herein.

Program instructions 12 implementing methods such as those described herein may be transmitted over or stored on computer-readable medium 10. The computer-readable medium may be a transmission medium such as a wire, cable, or wireless transmission link. The computer-readable medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using ActiveX controls, C++ objects, Java- Beans, Matlab, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 2:
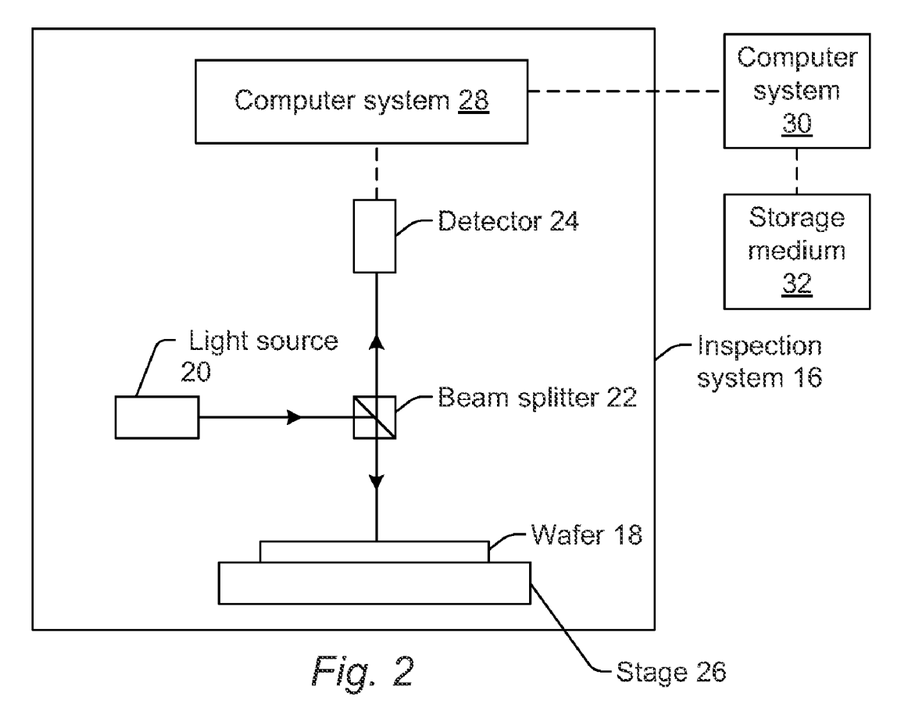
FIG. 2 is a schematic diagram illustrating a side view of one embodiment of a system configured to generate information to be used for selecting values for one or more parameters of a detection algorithm.

An additional embodiment relates to a system configured to generate information to be used for selecting values for one or more parameters of a detection algorithm. The system includes an inspection system configured to perform a scan of an area of a wafer using default values for one or more parameters of a detection algorithm to detect defects on the wafer. One embodiment of such a system is shown in FIG. 2. For example, as shown in FIG. 2, the system includes inspection system 16. Inspection system 16 is configured to perform a scan of an area of wafer 18.

In one embodiment, inspection system 16 includes light source 20. Light source may include any appropriate light source known in the art. Light source 20 may be configured to direct light to beam splitter 22. Beam splitter 22 may be configured to direct light from light source 20 to wafer 18 at a substantially normal angle of incidence. Beam splitter 22 may include any appropriate optical component known in the art.

Light reflected from wafer 18 may pass through beam splitter 22 to detector 24. Detector 24 may include any appropriate detector known in the art. Output generated by detector 24 may be used to detect defects on wafer 18. For example, inspection system 16 may include computer system 28 configured to detect defects on wafer 18 by applying the detection algorithm to output generated by the detector. The computer system may use the default values for the one or more parameters of the detection algorithm to detect defects on the wafer according to any of the embodiments described herein. The default values for the one or more parameters of the detection algorithm may include any of the default values described herein. The detection algorithm may include any of the detection algorithms described herein. The computer system may be coupled to the detector in any suitable manner (e.g., by one or more transmission media indicated by the dashed line shown in FIG. 2, which may include any suitable transmission media known in the art) such that the computer system can receive the output generated by the detector. Furthermore, if the inspection system includes more than one detector (not shown), the computer system may be coupled to each detector as described above. Computer system 28 may be further configured as described herein.

During inspection, wafer 18 may be disposed on stage 26. Stage 26 may include any appropriate mechanical and/or robotic assembly known in the art. The inspection system may be configured to perform the scan of the area of the wafer by scanning the light over the area of the wafer while detecting the light reflected by the wafer in any suitable manner known in the art (e.g., by moving the stage and therefore the wafer with respect to the light). The scan of the wafer may be further performed by the inspection system according to any of the embodiments described herein. The area of the wafer includes an entire area of the wafer that will be scanned using an inspection recipe. The inspection recipe may include any of the inspection recipes described herein. In addition, the scan is performed without user intervention. The scan may be performed without user intervention according to any of the embodiments described herein. The inspection system shown in FIG. 2 may also include any other suitable components (not shown) known in the art.

As shown in FIG. 2, the inspection system is configured to detect light specularly reflected from the wafer. In this manner, the inspection system shown in FIG. 2 is configured as a BF inspection system. However, the inspection system may be replaced by an inspection system configured as a DF inspection system, an edge contrast (EC) inspection system, an aperture mode inspection system, or any other optical inspection system known in the art. In addition, the inspection system may be configured to perform one or more inspection modes. For example, the inspection system show in FIG. 2 may be configured to perform DF inspection by altering an angle of incidence at which the light is directed to the wafer and/or an angle at which light is collected from the wafer. In another example, the inspection system shown in FIG. 2 may be configured such that one or more optical components (not shown) such as apertures may be positioned in the illumination path and the collection path such that the inspection system can perform EC mode inspection and/or an aperture mode of inspection.

It is noted that FIG. 2 is provided herein to generally illustrate one configuration of an inspection system that may be included in the system embodiments described herein. Obviously, the inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system) such as the 236x and 28xx series of tools and the Puma 9000 and 9100 series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

In another embodiment, the optical inspection system shown in FIG. 2 may be replaced by an electron beam inspection system. Examples of commercially available electron beam inspection systems that may be included in the system of FIG. 2 include the eS25. eS30, and eS31 systems from KLA-Tencor.

The system also includes computer system 30 configured to select a portion of the defects from results of the scan based on a predetermined maximum number of total defects to be used for selecting values for the one or more parameters of the detection algorithm. For example, computer system 30 may be coupled to computer system 28 in any suitable manner (e.g., by one or more transmission media, that serve as a "data link" between the two computer systems) such that computer system 30 can receive the results of the scan from computer system 28. The results of the scan may include any of the results of the scan described herein. Computer system 30 may be configured to select the portion of the defects according to any of the embodiments described herein.

In some embodiments, the defect down sampling recipe (to select a portion of the defects) is automatically generated by computer system 30 and then applied by computer system 28 during the final scan to keep defects above thresholds for each bin. In some such embodiments, during the final scan, defects below thresholds for each bin are discarded by computer system 28 such that computer system 28 functions smoothly without causing system choking while at the same time, detecting enough defects at and below the noise floor for later recipe tuning using the OSTS final lot, which may be performed by computer system 30.

Computer system 30 is also configured to store information for the portion of the defects. For example, the computer system may be configured to store the information for the portion of the defects in storage medium 32. The storage medium may include any of the storage media described herein or any other suitable storage media known in the art. The storage medium may be external to the computer system as shown in FIG. 2. Alternatively, the storage medium may be internal to the computer system. The computer system may be configured to store the information as described herein or in any other suitable manner. The information includes values for the one or more parameters of the detection algorithm determined for the defects in the portion. The information may include any such information described herein, possibly in combination with any other information described herein. The information can be used to select the values for the one or more parameters of the detection algorithm to be used for the inspection recipe without performing an additional scan of the wafer subsequent to the scan. The information can be used to select the values for the one or more parameters according to any of the embodiments described herein.

Computer system 30 may be configured as a stand-alone system that does not form part of a process, inspection, metrology, review, or other tool. As described above, computer system 30 may be configured to receive and/or acquire data or information from other systems (e.g., results of the scan from the inspection system) by a transmission medium that may include "wired" and/or "wireless" portions. In this manner, the transmission medium may serve as a data link between the computer system and the other system. In addition, computer system 30 may send data to another system via the transmission medium. Such data may include, for example, the values for the one or more parameters of the detection algorithm to be used for the inspection recipe. Alternatively, computer system 30 may form part of the inspection system. In addition, computer system 28 may be configured to perform one or more of the steps that computer system 30 is configured to perform as described above.

The embodiments of the system shown in FIG. 2 may be further configured as described herein. In addition, the system may be configured to perform any step(s) of any of the method embodiment(s) described herein.

Further modifications and alternative embodiments of various aspects of the invention may be apparent to those skilled in the art in view of this description. For example, methods and systems for generating information to be used for selecting values for one or more parameters of a detection algorithm are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for generating information to be used for selecting values for one or more parameters of a detection algorithm, comprising:

performing a scan of an area of a wafer using an inspection system and default values for one or more parameters of a detection algorithm to detect defects on the wafer, wherein the area of the wafer comprises an entire area of the wafer that will be scanned using an inspection recipe, and wherein the scan is performed without user intervention;

selecting a portion of the defects from results of the scan based on a predetermined maximum number of total defects to be used for selecting values for the one or more parameters of the detection algorithm; and storing information for the portion of the defects, wherein the information comprises values for the one or more parameters of the detection algorithm determined for the defects in the portion, and wherein the information can be used to select the values for the one or more parameters of the detection algorithm to be used for the inspection recipe without performing an additional scan of the wafer subsequent to the scan.

2. The method of claim 1, further comprising prior to performing the scan, performing an initial scan of the wafer using the inspection system and default values for the one or more parameters of the detection algorithm and determining one or more parameters of said selecting based on results of the initial scan, wherein the initial scan and said determining are performed without user intervention.

3. The method of claim 1, further comprising prior to performing the scan, performing an initial scan of the wafer using the inspection system and default values for the one or more parameters of the detection algorithm and determining one or more parameters of said selecting based on results of the initial scan, wherein the initial scan and the scan are performed sequentially without input from a user between the initial scan and the scan.

4. The method of 1, further comprising generating a multi-dimensional histogram for values for two or more of the parameters of the detection algorithm determined for defects detected during an initial scan performed prior to performing the scan and determining one or more parameters to be used for said selecting based on the multi-dimensional histogram, total number of the defects detected by the initial scan, the predetermined maximum number of the total defects to be used for selecting the values for the one or more parameters of the detection algorithm, the entire area of the wafer that will be scanned using the inspection recipe, and an area of the wafer scanned during the initial scan.

5. The method of claim 4, wherein the values for the two or more of the parameters of the detection algorithm determined for the defects detected during the initial scan comprise values for threshold offset and median reference intensity, and wherein information about the defects detected during the initial scan other than the multi-dimensional histogram and the total number of the defects detected by the initial scan is not saved.

6. The method of claim 1, wherein performing the scan without the user intervention comprises performing the scan without input from a user for the default values for the one or more parameters of the detection algorithm and without input from the user for any other one or more parameters of the inspection recipe.

7. The method of claim 1, wherein the default values for the one or more parameters of the detection algorithm used for the scan comprise a default value for a threshold applied to output generated by the scan to detect the defects on the wafer, and wherein the default value for the threshold is at or below a noise floor of the output generated by the scan.

8. The method of claim 1, wherein selecting the portion of the defects comprises selecting the defects having larger values for the one or more parameters of the detection algorithm than other defects.

9. The method of claim 1, wherein selecting the portion of the defects comprises selecting the same number of defects for a substantial portion of bins in a multi-dimensional histogram for the values for two or more of the parameters of the detection algorithm.

10. The method of claim 1, wherein the one or more parameters of the detection algorithm comprise frames, segments, and regions, and wherein the predetermined maximum number of total defects comprises only one defect per frame per segment per region.

11. The method of claim 1, wherein the values for the one or more parameters that can be selected without requiring the additional scan of the wafer comprise values for segment breaks.

12. The method of claim 1, wherein the values for the one or more parameters that can be selected without requiring the additional scan of the wafer comprise values for segment breaks and values for thresholds for segments, and wherein the values for the segment breaks and the thresholds can be selected simultaneously.

13. The method of claim 1, wherein the values for the one or more parameters of the detection algorithm determined for the defects comprise triggered threshold offset and median intensity value.

14. The method of claim 1, wherein the information further comprises a multi-dimensional histogram for the values for two or more of the parameters of the detection algorithm determined for defects in the portion.

15. The method of claim 1, wherein the information further comprises patch images for the defects in the portion acquired by the inspection system during the scan.

16. The method of claim 1, wherein the information can be used to select the values for all parameters of the detection algorithm without performing the additional scan of the wafer subsequent to the scan.

17. The method of claim 1, wherein the inspection recipe comprises an inspection recipe for bright field inspection of the wafer.

18. The method of claim 1, wherein the inspection recipe comprises an inspection recipe for dark field inspection of the wafer.

19. A non-transitory computer-readable medium containing computer instructions stored therein for causing a computer system to perform a method for generating information to be used for selecting values for one or more parameters of a detection algorithm, wherein the method comprises:
   performing a scan of an area of a wafer using an inspection system and default values for one or more parameters of a detection algorithm to detect defects on the wafer, wherein the area of the wafer comprises an entire area of the wafer that will be scanned using an inspection recipe, and wherein the scan is performed without user intervention;
   selecting a portion of the defects from results of the scan based on a predetermined maximum number of total defects to be used for selecting values for the one or more parameters of the detection algorithm; and
   storing information for the portion of the defects, wherein the information comprises values for the one or more parameters oldie detection algorithm determined for the defects in the portion, and wherein the information can be used to select the values for the one or more parameters of the detection algorithm to be used for the inspection recipe without performing an additional scan of the wafer subsequent to the scan.

20. A system configured to generate information to be used for selecting values for one or more parameters of a detection algorithm, comprising:
   an inspection system configured to perform a scan of an area of a wafer using default values for one or more parameters of a detection algorithm to detect defects on the wafer, wherein the area of the wafer comprises an entire area of the wafer that will be scanned using an inspection recipe, and wherein the scan is performed without user intervention; and
   a computer system configured to:
      select a portion of the defects from results of the scan based on a predetermined, maximum number of total defects to be used for selecting values for the one or more parameters of the detection algorithm; and
      store information for the portion of the defects, wherein the information comprises values for the one or more parameters of the detection algorithm determined for the defects in the portion, and wherein the information can be used to select the values for the one or more parameters of the detection algorithm to be used for the inspection recipe without performing an additional scan of the wafer subsequent to the scan.

* * * * *